(12) United States Patent
Clark et al.

(10) Patent No.: US 9,901,384 B2
(45) Date of Patent: Feb. 27, 2018

(54) AIRWAY DIAGNOSIS AND TREATMENT DEVICES AND RELATED METHODS OF USE

(71) Applicant: Boston Scientific Scimed, Inc., Maple Grove, MN (US)

(72) Inventors: Bryan Allen Clark, Forest Lake, MN (US); Aiden Flanagan, Kilcolgan (IE); Michael Eppihimer, Franklin, MA (US); William Conrad Stoffregen, Lake Elmo, MN (US); Juan Gabriel Hincapie Ordonez, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/083,720

(22) Filed: Mar. 29, 2016

(65) Prior Publication Data
US 2016/0287307 A1 Oct. 6, 2016

Related U.S. Application Data

(60) Provisional application No. 62/140,860, filed on Mar. 31, 2015.

(51) Int. Cl.
*A61B 18/00* (2006.01)
*A61B 5/08* (2006.01)
(Continued)

(52) U.S. Cl.
CPC ............... *A61B 18/00* (2013.01); *A61B 5/08* (2013.01); *A61B 5/4836* (2013.01);
(Continued)

(58) Field of Classification Search
CPC ....... A61B 5/08; A61B 5/4836; A61B 5/4848; A61B 5/4884; A61B 5/6852;
(Continued)

(56) References Cited

U.S. PATENT DOCUMENTS

| 8,088,127 B2 | 1/2012 | Mayse et al. |
| 2003/0233099 A1 | 12/2003 | Danaek et al. |

(Continued)

FOREIGN PATENT DOCUMENTS

| WO | WO 2009/137819 A1 | 11/2009 |
| WO | WO 2011/060201 A1 | 5/2011 |

OTHER PUBLICATIONS

Van Den Berge et al., "Clinical and inflammatory determinants of bronchial hyperresponsiveness in COPD", 2012, pp. 1098-1105, vol. 40, No. 5, European Respiratory Journal (8 pages).

(Continued)

*Primary Examiner* — Paula J Stice
(74) *Attorney, Agent, or Firm* — Bookoff McAndrews, PLLC

(57) ABSTRACT

A medical device may include a stimulation member configured to apply a stimulus to a nerve that is configured to control a contraction of an airway distal to the nerve, and a measurement member configured to measure an effect of the stimulus on the airway. The medical device also may include an energy delivery element configured to deliver energy to tissue defining the airway to reduce an effect of the stimulus on the airway. The energy delivery element may be disposed at or distally of the stimulation member.

20 Claims, 8 Drawing Sheets

(51) Int. Cl.
*A61B 5/00* (2006.01)
*A61N 1/36* (2006.01)
*A61N 1/05* (2006.01)
*A61B 18/14* (2006.01)

(52) U.S. Cl.
CPC .......... *A61B 5/4848* (2013.01); *A61B 5/4884* (2013.01); *A61B 5/6852* (2013.01); *A61N 1/0519* (2013.01); *A61N 1/3601* (2013.01); *A61N 1/3611* (2013.01); *A61B 5/6853* (2013.01); *A61B 5/6858* (2013.01); *A61B 18/1492* (2013.01); *A61B 2018/00434* (2013.01); *A61B 2018/00541* (2013.01); *A61B 2018/00642* (2013.01); *A61N 1/36053* (2013.01)

(58) Field of Classification Search
CPC ................ A61B 5/6853; A61B 5/6858; A61B 2018/00541; A61B 2015/0642; A61N 1/0519; A61N 1/3601; A61N 1/3611; A61N 1/36053
See application file for complete search history.

(56) References Cited

U.S. PATENT DOCUMENTS

| | | | |
|---|---|---|---|
| 2006/0254600 A1 | 11/2006 | Danek et al. | |
| 2012/0143099 A1 | 6/2012 | Daniels et al. | |
| 2012/0302909 A1* | 11/2012 | Mayse | A61B 5/411 600/532 |
| 2013/0289556 A1 | 10/2013 | Mayse et al. | |
| 2014/0148635 A1 | 5/2014 | Danek et al. | |
| 2015/0245867 A1* | 9/2015 | Gross | A61B 5/0215 606/34 |

OTHER PUBLICATIONS

College of Veterinary Medicine, Michigan State University, "Mechanism of Action of Bronchodilator Drugs", accessed Mar. 29, 2015, <http://cvm.msu.edu/research/research-labs/equine-pulmonary-laboratory/respiratory-diseases/heaves/mechanism-of-action-of-bronchodilator-drugs> (2 pages).

Barnes et al., "Neural and Humoral Control of the Airways", chapter 32 of "Asthma and COPD: Basic Mechanisms and Clinical Management", 2009, pp. 381-88, $2^{nd}$ Edition, Elsevier Ltd.

Undem et al., "Autonomic Neural Control of Intrathoracic Airways", Apr. 2012, pp. 1241-1267, vol. 2, Comprehensive Physiology, American Physiological Society (27 pages).

Wine, Jeffrey J., "Parasympathetic Control of Airway Submucosal Glands: Central Reflexes and the Airway Intrinsic Nervous System", Apr. 30, 2007, pp. 35-54, vol. 133, No. 1, The International Society of Autonomic Neuroscience (32 pages).

Canning, Brendan J., "Reflex regulation of airway smooth muscle tone", Sep. 2006, pp. 971-985, vol. 101, Journal of Applied Physiology, American Physiological Society (16 pages).

Undem et al., "The Role of Vagal Afferent Nerves in Chronic Obstructive Pulmonary Disease", 2005, pp. 355-360, vol. 2, Proceedings of the American Thoracic Society (6 pages).

Gosens et al., "Muscarinic receptor signaling in the pathophysiology of asthma and COPD", May 9, 2006, vol. 7, No. 73, Respiratory Research (15 pages).

Hoffmann et al., "Inhibition of Histamine-Induced Bronchoconstriction in Guinea Pig and Swine by Pulsed Electrical Vagus Nerve Stimulation", 2009, pp. 261-269, vol. 12, No. 4, International Neuromodulation Society (9 pages).

Undem et al., "Vagal innervation of guinea pig bronchial smooth muscle", 1990, pp. 1336-1346, American Physiological Society (11 pages).

* cited by examiner

AIRWAY DIAGNOSIS AND TREATMENT DEVICES AND RELATED METHODS OF USE

CROSS-REFERENCE TO RELATED APPLICATION(S)

This patent application claims benefit of priority under U.S.C. § 119 to U.S. Provisional Patent Application No. 62/140,860, filed Mar. 31, 2015, the entirety of which is incorporated herein by reference.

TECHNICAL FIELD

Various examples of the present disclosure relate generally to medical devices and related methods of use. More specifically, the present disclosure relates to airway diagnosis and treatment devices, systems, and methods for diagnosing and treating the lung.

BACKGROUND

Chronic obstructive pulmonary disease (COPD) includes conditions such as, e.g., chronic bronchitis and emphysema. COPD currently affects over 15 million people in the United States alone and is currently the third leading cause of death in the country. The primary cause of COPD is the inhalation of cigarette smoke, responsible for over 90% of COPD cases. The economic and social burden of the disease is substantial and is increasing.

Chronic bronchitis is characterized by chronic cough with sputum production. Due to airway inflammation, mucus hypersecretion, airway hyperresponsiveness, and eventual fibrosis of the airway walls, significant airflow and gas exchange limitations result.

Emphysema is characterized by the destruction of the lung parenchyma. This destruction of the lung parenchyma leads to a loss of elastic recoil and tethering which maintains airway patency. Because bronchioles are not supported by cartilage like the larger airways, they have little intrinsic support and therefore are susceptible to collapse when destruction of tethering occurs, particularly during exhalation.

Acute exacerbations of COPD (AECOPD) often require emergency care and inpatient hospital care. An AECOPD is defined by a sudden worsening of symptoms (e.g., increase in or onset of cough, wheeze, and sputum changes) that typically last for several days, but can persist for weeks. An AECOPD is typically triggered by a bacterial infection, viral infection, or pollutants, which manifest quickly into airway inflammation, mucus hypersecretion, and bronchoconstriction, causing significant airway restriction.

Despite relatively efficacious drugs (long-acting muscarinic antagonists, long-acting beta agonists, corticosteroids, and antibiotics) that treat COPD symptoms, a particular segment of patients known as "frequent exacerbators" often visit the emergency room and hospital with exacerbations and also have a more rapid decline in lung function, poorer quality of life, and a greater mortality risk.

Reversible obstructive pulmonary disease includes asthma and reversible aspects of COPD. Asthma is a disease in which bronchoconstriction, excessive mucus production, and inflammation and swelling of airways occur, causing widespread but variable airflow obstruction thereby making it difficult for the asthma sufferer to breathe. Asthma is further characterized by acute episodes of airway narrowing via contraction of hyper-responsive airway smooth muscle.

The reversible aspects of COPD include excessive mucus production and partial airway occlusion, airway narrowing secondary to smooth muscle contraction, and bronchial wall edema and inflation of the airways. Usually, there is a general increase in bulk (hypertrophy) of the large bronchi and chronic inflammatory changes in the small airways. Excessive amounts of mucus are found in the airways, and semisolid plugs of mucus may occlude some small bronchi. Also, the small airways are narrowed and show inflammatory changes.

In asthma, chronic inflammatory processes in the airway play a central role in increasing the resistance to airflow within the lungs. Many cells and cellular elements are involved in the inflammatory process including, but not limited to, mast cells, eosinophils, T lymphocytes, neutrophils, epithelial cells, and even airway smooth muscle itself. The reactions of these cells result in an associated increase in sensitivity and hyperresponsiveness of the airway smooth muscle cells lining the airways to particular stimuli.

The chronic nature of asthma can also lead to remodeling of the airway wall (i.e., structural changes such as airway wall thickening or chronic edema) that can further affect the function of the airway wall and influence airway hyper-responsiveness. Epithelial denudation exposes the underlying tissue to substances that would not normally otherwise contact the underlying tissue, further reinforcing the cycle of cellular damage and inflammatory response.

In susceptible individuals, asthma symptoms include recurrent episodes of shortness of breath (dyspnea), wheezing, chest tightness, and cough. Currently, asthma is managed by a combination of stimulus avoidance and pharmacology.

The autonomic nervous system (ANS) provides constant control over airway smooth muscle, secretory cells, and vasculature. The ANS is divided into two subsystems, the parasympathetic nervous system and the sympathetic nervous system. These two systems operate independently for some functions, and cooperatively for other functions. The parasympathetic system is responsible for the unconscious regulation of internal organs and glands. In particular, the parasympathetic system is responsible for sexual arousal, salivation, lacrimation, urination, and digestion, among other functions. The sympathetic nervous system is responsible for stimulating activities associated with the fight-or-flight response. Although both sympathetic and parasympathetic branches of the ANS innervate lung airways, it is the parasympathetic branch that dominates with respect to control of airway smooth muscle, bronchial blood flow, and mucus secretions.

FIG. 1 illustrates the cholinergic control of airway smooth muscle and submucosal glands. An airway 100 may include an inner surface 102 that includes epithelial tissue 104. A nerve fiber 106 may include a plurality of receptors 108 that are disposed within epithelial tissue 104. Nerve fibers 106 may be C-fibers having receptors 108 disposed within epithelial tissue 104. Nerve fibers 106 may be afferent (sensory) nerves that carry nerve impulses from receptors 108 toward central nervous system (CNS) 109. Receptors 108 may respond to a wide variety of chemical stimuli and other irritants, such as, e.g., cigarette smoke, histamine, bradykinin, capsaicin, allergens, and pollens. C-fibers can also be triggered by autocoids that are released upon damage to tissues of the lung. The stimulation of receptors 108 by the various stimuli elicits reflex cholinergic bronchoconstriction.

Parasympathetic innervation of the airways is carried exclusively by vagus nerve 110 (e.g., the right and left vagus nerves). Upon receiving a signal from nerve fiber 106, CNS 109 may send a signal to initiate bronchoconstriction and/or mucus secretion. Cholinergic nerve fibers (e.g., nerve fibers that use acetylcholine (ACh) 120 as their neurotransmitter) arise in the nucleus ambiguous in the brain stem and travel down a vagus nerve 110 (right and left vagus nerves) and synapse in parasympathetic ganglia 112 which are located within the airway wall. These parasympathetic ganglia are most numerous in the trachea and mainstem bronchi, especially near the hilus and points of bifurcations, with fewer ganglia that are smaller in size dispersed in distal airways. From these ganglia, short post-ganglionic fibers 114 travel to airway smooth muscle 116 and submucosal glands 118. Ach 120, the parasympathetic neurotransmitter, is released from post-ganglionic fibers and acts upon M1- and M3-receptors on smooth muscles 116 and submucosal glands 118 to cause bronchoconstriction (via constriction of smooth muscles 116), and the secretion of mucus 122 within airway 100 by submucosal glands 118, respectively. Ach 120 may additionally regulate airway inflammation and airway remodeling, and may contribute significantly to the pathophysiology of obstructive airway diseases. Thus, fibers 114 may be efferent fibers (motor or effector neurons) that are configured to carry nerve impulses away from CNS 109.

FIG. 2 illustrates additional afferent nerve fibers located in airway 100 and in airway smooth muscle 116. Airway 100 may include one or more nerve fibers 106 and receptors 108 as described with reference to FIG. 1. Additionally, one or more nerve fibers 206 having one or more receptors 208 may be disposed within epithelial tissue 104. Nerve fibers 206 may be myelinated Rapidly Adapting Receptors (RAR) that respond to mechanical stimuli and are responsible in part for bronchoconstriction. Receptors 208 may respond to mechanical stimuli such as, e.g., water, airborne particulates, mucus, and the stretching of the lung during breathing or coughing. RARs may cause bronchoconstriction and are triggered by mechano-stimulation (e.g., mechanical pressure or distortion) and/or chemo-stimulation. Additionally, RARs may be triggered secondary to bronchoconstriction, leading to an amplification of the constriction response.

Airway smooth muscle 116 may be coupled to one or more receptors 210. Receptors 210 may be, e.g., Slowly Adapting Receptors (SARs) that are coupled to one or more nerve fibers 211.

Bronchial hyperresponsivity (BHR) may be present in a considerable number of COPD patients. Various reports have suggested BHR to be present in between ~60% and 94% of COPD patients. This "hyperresponsivity" could be due to a "hyperreflexivity." However there are several logical mechanisms by which parasympathetic drive may be overactivated in inflammatory disease. First, inflammation is commonly associated with overt activation and increases in excitability of vagal C-fibers in the airways that could increase reflex parasympathetic tone. Secondly, airway inflammation and inflammatory mediators have been found to increase synaptic efficacy and decrease action potential accommodation in bronchial parasympathetic ganglia, effects that would likely reduce their filtering function and lead to prolonged excitation. Thirdly, airway inflammation has also been found to inhibit muscarinic M2 receptor-mediated auto-inhibition of ACh release from postganglionic nerve terminals. This would lead to a larger end-organ response (e.g., smooth muscle contraction) per a given amount of action potential discharge. Fourthly, airway inflammation has been associated with phenotypic changes in the parasympathetic nervous system that could affect the balance of cholinergic contractile versus non-adrenergic non-cholinergic (NANC) relaxant innervation of smooth muscle.

Because airway resistance varies inversely with the fourth power of the airway radius, BHR is believed to be a function of both bronchoconstriction and inflammation. Inflammation in the airway walls reduces the inner diameter (or radius) of the airway lumen, thus amplifying the effect of even baseline cholinergic tone, because for a given change in muscle contraction, the airway lumen will close to a greater extent. BHR is likely caused by hypersensitivity of receptor nerve fibers, such as, e.g., C-fibers, RAR fibers, SAR fibers, and the like, lower thresholds for reflex action initiation, and reduced self-limitation of acetylcholine release.

The majority of vagal afferent nerves in the lungs are nociceptors that are adept at sensing the type of tissue injury and inflammation that occurs in the lungs in COPD. In addition, stretch sensitive afferent nerves are present in the lungs and can be activated by the tissue distention that occurs during eupneic (normal) breathing. The pattern of action potential discharge in these fibers depends on the rate and depth of breathing, the lung volume at which respiration is occurring, and the compliance of the lungs. Therefore, because COPD patients exhibit impaired breathing, the activity of nociceptive and mechano-sensitive afferent nerves is grossly altered in patients with COPD. The distortion in vagal afferent nerve activity in COPD may lead to situations where these responses are out of sync with the body's needs.

Thus, a need exists for patients suffering from diseases of the lung.

SUMMARY OF THE DISCLOSURE

The present disclosure includes devices for diagnosing and treating airways and related methods of use.

In one aspect, the present disclosure is directed to a medical device. The medical device may include a stimulation member configured to apply a stimulus to a nerve that is configured to control a contraction of an airway distal to the nerve, and a measurement member configured to measure an effect of the stimulus on the airway. The medical device also may include an energy delivery element configured to deliver energy to tissue defining the airway to reduce an effect of the stimulus on the airway. The energy delivery element may be disposed at or distally of the stimulation member.

The measurement member and energy delivery element may be disposed on or incorporated into an expandable member. The expandable member may include a basket, stent, balloon, or umbrella. The expandable member may be configured to absorb heat from tissues defining the airway. The stimulation member may be disposed at a distal end of a first elongate member, and the energy delivery element may be disposed on a second elongate member that extends distally from the first elongate member. The stimulation member may be configured to deliver a stimulus agent to the treatment location. The stimulus agent may include one or more of methacholine, histamine, bradykinin, adenosine, mannitol, and capsaicin. The energy delivery element may include an expandable stent, basket, balloon, or umbrella, and the stimulation member may be disposed within the expandable stent, basket, balloon, or umbrella. The stimulation member may be configured to deliver non-therapeutic electrical energy to lung tissue. The energy delivery element may be configured to deliver therapeutic electrical energy to lung tissue. The stimulation member may be configured to deliver non-therapeutic electrical energy from outside of a patient, transcutaneously through the skin of the patient, to a nerve disposed within a neck of the patient. The stimulation member and the energy delivery element may be disposed on or incorporated into an expandable member. The expandable member may be configured to deliver non-therapeutic electrical energy in a stimulus mode, and therapeutic electrical energy in a therapy mode. The measurement member may include an imaging device configured to determine a contraction level of the airway or a diameter of the airway. The medical device also may include a first elongate member, and a second elongate member extending distally from the first elongate member. The energy delivery element may be disposed at a distal end of the second elongate member.

In another aspect, the present disclosure is directed to a method of treating a lung. The method may include applying stimulus to a nerve at a stimulation location, and measuring an effect of the stimulus on an airway of the lung. The airway may be spaced apart from or distal to the stimulation location. The method also may include selecting a treatment location in the lung based on the measured effect of the stimulus on the airway, and applying therapeutic energy to lung tissue at the treatment location.

The nerve may regulate lung airway constriction. The nerve may be a vagus nerve. The vagus nerve may be stimulated at a location distal to cardiac branches of the vagus nerve. The stimulus may be applied by a stimulation member, through tissues of the lung, to the nerve. The stimulus may be applied by a stimulation member disposed outside of a patient, transcutaneously through the skin of the patient, to the nerve. The stimulus may be non-therapeutic electrical energy. The stimulus may be an agent configured to activate the nerve to induce constriction of the lung airway. The agent may be one or more of methacholine, histamine, bradykinin, adenosine, mannitol, and capsaicin. Measuring the effect of the stimulus on the airway may include measuring an amount the airway constricts in response to the stimulus. The treatment location may be proximal to the airway. The treatment location may be the stimulation location. The treatment location may be distal to the stimulation location. The treatment location may proximal to the airway, and may be distal to the stimulation location. Selecting the treatment location based on the measured effect of the stimulus on the airway, may include selecting the stimulation location as the treatment location if the measured effect of the stimulus on the airway is greater than a threshold value. The threshold value may include one or more of a minimum contraction level, a minimum force level, a minimum airway diameter, and a minimum airflow value. The method may further include applying an additional stimulus to the stimulation location after applying therapeutic energy to the treatment location, and measuring the effect of the additional stimulus on the airway. The method may further include re-applying therapeutic energy to the treatment location if the measured effect of the additional stimulus exceeds the threshold value. The treatment location may be the airway. Selecting the treatment location based on the measured effect of the stimulus on the airway, may include selecting the airway as the treatment location if the measured effect of the stimulus on the airway is greater than a threshold value.

According to yet another aspect, the present disclosure is directed to a method of treating a lung. The method may include applying a first stimulus to a first stimulation location, and measuring an effect of the first stimulus on an airway of the lung. The airway may be distal to the first stimulation location. The method also may include applying a second stimulus to a second stimulation location, and measuring an effect of the second stimulus on the airway. The method also may include applying therapeutic energy to the first stimulation location and/or second stimulation location based on the measured effect of the first stimulus and second stimulus on the airway.

The method also may include applying therapeutic energy to the first stimulation location if the measured effect on the airway is greater resulting from the first stimulus as compared to the second stimulus.

According to yet another aspect, the present disclosure is directed to a method of treating a lung. The method may include applying stimulus to a nerve at a stimulation location, and measuring an effect of the stimulus on an airway of the lung. The airway may be spaced apart from or distal to the stimulation location. The method also may include selecting a treatment location in the lung based on the measured effect of the stimulus on the airway. The treatment location may be offset from the stimulation location. The method also may include applying therapeutic energy to lung tissue at the treatment location

BRIEF DESCRIPTION OF THE FIGURES

The accompanying drawings, which are incorporated in and constitute a part of this specification, illustrate various exemplary examples and together with the description, serve to explain the principles of the disclosed examples.

DETAILED DESCRIPTION

Reference will now be made in detail to examples of the present disclosure, examples of which are illustrated in the accompanying drawings. Wherever possible, the same reference numbers will be used throughout the drawings to refer to the same or like parts.

Figure 3:
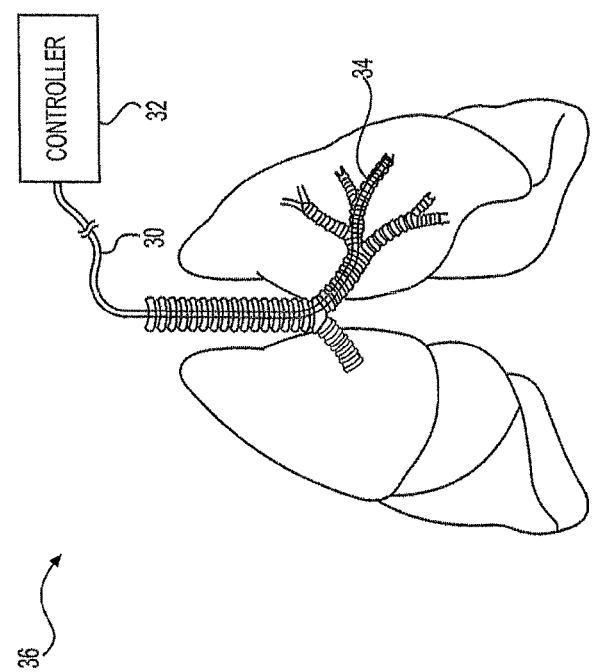
FIG. 3 is a schematic view of the lungs being treated with a treatment device according to an example of the present disclosure.

FIG. 3 is an illustration of a lung being treated with a system 36 according to the present disclosure. The system 36 may include a controller 32 and a delivery device 30 which may be an elongated member as described further below. The delivery device 30 may include a tool that can be positioned at a treatment site 34 within a lung or another target medium.

In some examples, the controller 32 may include a processor that is generally configured to accept information from the system and system components, and process the information according to various algorithms to produce control signals for controlling the delivery device 30. The processor may accept information from the system and system components, process the information according to various algorithms, and produce information signals that may be directed to visual indicators, digital displays, audio tone generators, or other indicators of, e.g., a user interface, in order to inform a user of the system status, component status, procedure status or any other useful information that is being monitored by the system. The processor may be a digital IC processor, analog processor or any other suitable logic or control system that carries out the control algorithms.

Figure 1:
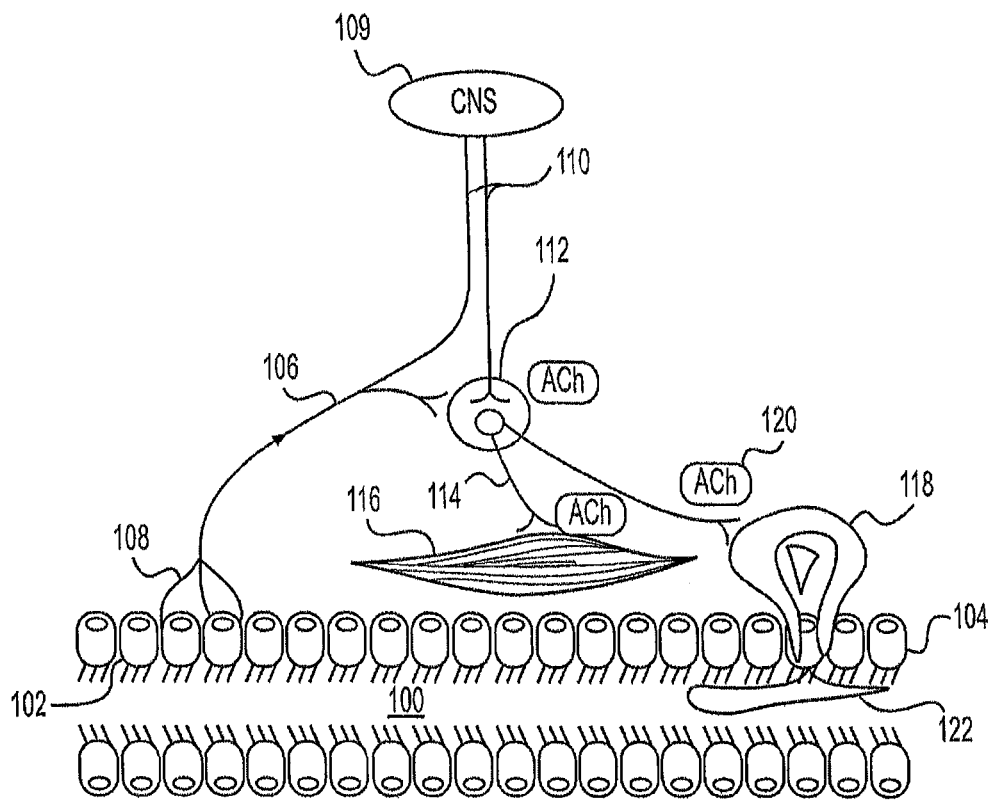
FIG. 1 is a schematic view of an airway and a cholinergic pathway.
Figure 2:
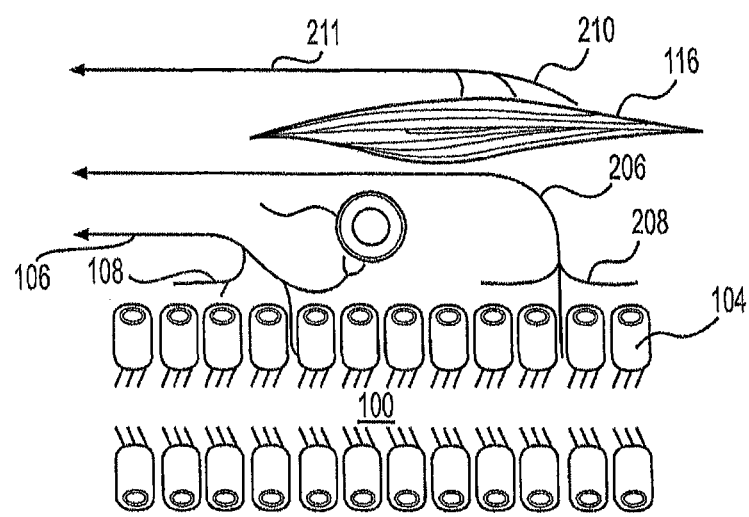
FIG. 2 is a schematic view of an airway and afferent nerves.
Figure 4:
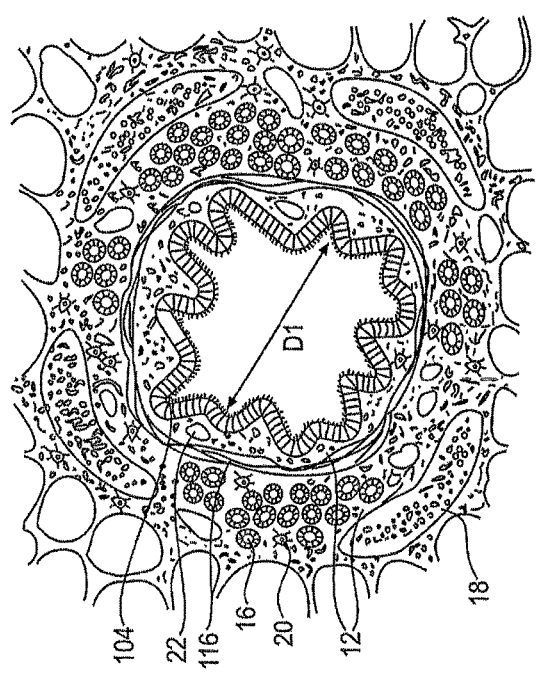
FIG. 4 is a cross-sectional view of an airway in a healthy lung.

FIG. 4 illustrates a cross-section of an airway in a healthy patient. The airway of FIG. 2 may be a medium-sized bronchus having an airway diameter D1 of about 3 mm, although the airway may have another suitable diameter. The airway may include a folded inner surface or epithelial tissue 104 surrounded by stroma 12 and smooth muscle tissue 116. Epithelial tissue 104 may include afferent sensory nerves, among other nerves. The larger airways, including the bronchus shown in FIG. 1, may have mucous glands 16 and cartilage 18 surrounding the smooth muscle tissue 116. Nerve fibers 20 and blood vessels 22 may surround the airway. Nerve fibers 20 may include, e.g., both afferent and efferent nerves.

Denervation

In some examples, therapy delivered by medical devices of the present disclosure may reduce acute exacerbations in COPD patients through the reduction of bronchoconstriction and mucus secretion caused by parasympathetic nerve activity. In other examples, symptoms of asthma, cystic fibrosis, chronic cough, or other diseases of the lung may be reduced or eliminated. Additionally, a reduction in airway inflammation and remodeling may be achieved. In some examples, the therapy may result in a reduction in the release of acetylcholine (ACh) or inflammatory mediators (e.g., tachykinins) from nerves in the airways of the lung. Thus, less ACh may be available to bind to muscarinic M1- and M3- receptors on smooth muscle cells and submucosal glands in the lung, resulting in less bronchoconstriction and mucus production.

The examples of the present disclosure may impair the transmission of signals from nerves (e.g., afferent receptors, afferent fibers, efferent nerve cell bodies, efferent nerve trunks, efferent fibers, C-Fibers, RAR fibers, SAR fibers, or the like) in the epithelium or airway walls which evoke reflex bronchoconstriction responses when activated by irritants or stimulants. Stimulation of these nerves may evoke bronchoconstriction, mucus production, cough, and pulmonary edema through either pre-ganglionic parasympathetic activity (acting on the central nervous system) or post-ganglionic parasympathetic activity (acting directly on parasympathetic ganglia). Thus, examples of the present disclosure may direct therapies or treatments capable of damaging nerves of the lung sufficient to reduce an ability of those nerves to send nerve signals. For example, afferent receptors and nerve fibers may be impaired from sending nerve signals to the CNS, while efferent nerve fibers, nerve cell bodies, and nerve trunks may be impaired from sending nerve signals to, e.g., smooth muscle to evoke bronchoconstriction and mucus production, among other responses.

In some examples, selective and partial denervation of the bronchial sensory vagal afferent fibers, and in particular the C and RAR fibers having endings in the epithelial layer, may result in more stable or normal vagal afferent activity and nervous system input from the lung.

The interpretation or preprocessing of afferent signals in ganglia may filter the sensory input to the CNS. That is, thresholds may exist for signals to be allowed to pass to the CNS so that many nerves may need to fire within a time period for the signal to be transmitted. Also, secondary effects caused by the initial response can cause a greater intensity and amplification of the response. In some examples, reducing afferent input may cause an irritant response that would otherwise reach the threshold for passing to the CNS to fail to be perceived as reaching the threshold. Thus, in some examples, reducing afferent input from an area of the lung (e.g., upper airways, central airways, or lower airways) may result in a significant reduction in reflex bronchoconstriction. Thus, in some examples, a damaged nerve may require an increased amount of stimulus before sending a nerve signal to the central nervous system, as compared to a pre-damaged state of the nerve.

Nerves can be damaged in the right main bronchus, left main bronchus, or both, as treating only one of the right or left main bronchi may be sufficient for a significant reduction in bronchoconstriction, as the right and left vagus nerves traverse along the right and left main bronchi, respectively. Additionally or alternatively, nerves may be damaged in airways distal to the right main bronchus and/or left main bronchus. Additionally, the CNS may interpret signal from only one of the left side or right side of the lung as an anomaly, which may result in a reduced cholinergic reflex, reduced bronchoconstriction, and/or reduced mucus secretion response.

In some examples, bronchoconstriction and mucus secretion caused by reflex parasympathetic nerve activity may be reduced. In some examples, airway inflammation and remodeling also may be reduced. Sensations of breathlessness (e.g., dyspnea) may be reduced by eliminating some of the afferent activity contributing to the Hering-Breuer reflex, possibly reducing the occurrence of dynamic hyperinflation. By selectively destroying sensory nerves/irritant receptors in the airway, reflex-mediated bronchoconstriction response to various irritant stimuli (e.g., smoke, pollution, etc.) that often trigger acute exacerbations of COPD may be reduced.

The denervation may be superficial to lung airway surfaces and/or may be applied to a depth beyond lung airway surfaces, superficially on the lung airway surfaces, interstitially within the lung airway wall space, and outside the lung airway wall (as some nerve trunks are exterior to the lung airway wall). The target airways may be first to higher generation bronchi (e.g., up to the 10th generation bronchi or beyond). In some examples, it may be undesired to treat the trachea in order to preserve the cough reflex. In some examples, energy or an agent may be applied to the bronchial branch points (e.g., bifurcations or the like) where RAR fibers are common. Additionally, the concentration of irritants may be relatively high around the bronchial branch points, resulting in a higher nervous system response than other areas of the lung. Denervation may also occur deeper in the airway wall, where both afferent and efferent nerves may be disposed along nerve trunks.

Denervation can be partial, e.g., in many small areas along the airway, as a spiral, in a non-circumferential pattern, in a plurality of spotted treatments, or in another suitable pattern. By treating the airway in this manner, afferent activity may be reduced while allowing for a rapid recovery of the epithelium, and reduced inflammation. Also, the cough response may be reduced but not eliminated, and mucociliary action may be reduced for a short while but not eliminated. This may be advantageous over other denervation procedures that eliminate or substantially impair mucociliary action. This may also reduce the possibility of strictures forming or other adverse events from occurring. In some examples, these benefits also may be achieved by only treating the portion(s) of the airway diameter where the highest nerve density and/or nerve trunk is located. These regions may be identified prior to a procedure, or may be determined, by e.g., visual analysis. In one example, optical coherence tomography may be utilized to identify specific treatment regions. In other examples, autoflorescence, Raman scattering, infrared reflectivity, micro-anatomical cyto-architecture techniques, and/or biochemical analysis via inflammatory mediators or neurotransmitters, also may be used to identify or visualize anatomical structures such as nerves.

Figure 5:
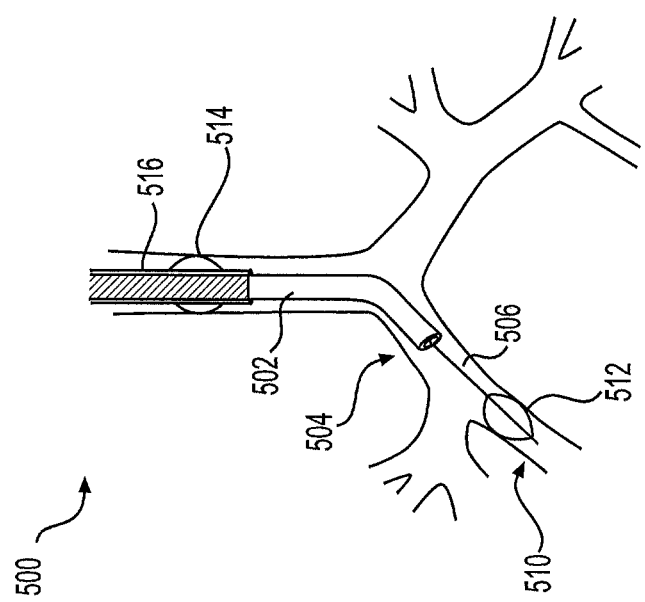
FIG. 5 is an in vivo illustration of a medical device in accordance with an example of the present disclosure.

A medical device 500 is shown in FIG. 5. Medical device 500 may include a first elongate member 502, such as, e.g., a bronchoscope, endoscope, or the like. A second elongate member 506 may be disposed at a distal end 504 of first elongate member 502. A therapy member 510 may be disposed at a distal end of second elongate member 506. Medical device 500 also may include a stimulation member 514 disposed on a sheath 516 that at least partially covers first elongate member 502. Stimulation member 514 may be disposed proximally of therapy delivery member 510.

Therapy member 510 may be an expandable member configured to reciprocally move between a collapsed configuration and an expanded configuration. Therapy member 510 may have larger dimensions (e.g., diameter, volume, and/or length) while in the expanded configuration as compared to the collapsed configuration. Therapy member 510 may be formed as any suitable expandable member, such as, e.g., a balloon, basket, stent, umbrella, or the like. Therapy member 510 also may include one or more energy delivery elements 512 that are configured to deliver energy to tissues of the body. In one example, energy delivery elements 512 may be RF electrodes, or an energy delivery element configured to deliver another type of energy modality, such as, e.g., HIFU, laser, cryotherapy, neurolytic, chemical modalities, or the like. In some examples, energy delivery elements 512 may be RF electrodes attached to an outer surface of the therapy member 510. In some examples, energy delivery elements 512 may be integrally formed with therapy member 510. Therapy member 510 may treat tissue by, for example, denervation, reducing airway smooth muscle, a combination of denervation and reduction of airway smooth muscle, and/or any other suitable treatment.

In the example of FIG. 5, therapy member 510 also may be a measurement member that is configured to measure a parameter of the lungs. For example, therapy member 510 may be configured to measure a strain or force of body tissues acting on therapy member 510 (e.g., a strain or force of lung airway walls acting on therapy member 510). Therapy member 510 may be placed against tissues defining a body lumen (e.g., a lung airway), and may contract as the walls of the airway contract and/or expand as the walls of the airway expand. Thus, once the airway contracts, the rate, magnitude, force, or any other characteristic of the contraction may be measured or assessed by therapy member 510. Therapy member 510 then may transmit information regarding the contraction of the walls of the airway using, for example, strain gauges. In another example, therapy member 510 may measure the diameter of an airway that therapy member 510 is disposed within. In another example, therapy member 510 may measure electrical signals (e.g., EMG, ENG) at a measurement location. In some examples, therapy member 510 may be configured to measure a parameter of an airway simultaneous to or after the stimulation of a nerve by stimulation member 514.

Although not shown, the contraction may be measured or assessed without making contact with the airway wall (e.g., visually with a retical; or optically, via a camera).

In another example, therapy member 510 may be a balloon catheter configured to measure contraction of an airway. As the airway constricts around the balloon, the balloon may increase in pressure. The pressure then may be characterized to determine the degree of contractile force acting on the balloon. The balloon also may include fluid inflow and outflow ports to inflate and deflate the balloon. The balloon also may be equipped with mechanisms to deliver an agent to the airway, or have electrodes to induce the contraction. The balloon may be configured to absorb heat from tissue defining the airway or otherwise surrounding the airway prior to, simultaneous with, or after energy delivery.

In another example, the measurement member may measure airflow at a location or near a location for treatment. The measurement member may be a hot-wire amenometer (not shown), where the airflow causes the heated wire to cool, and the rate of cooling of the wire may provide information regarding the airflow. The measurement member also may measure airflow resistance, mucus secretion, blood perfusion or blushing, or may measure acoustic signals, such as, e.g., wheezing. An airflow resistance measurement at any point in an airway may be an accumulation of resistance from alveoli to mouth, and thus, the measurement could be made outside the body via a tube connected to the mouth and/or a plethysmograph. In such examples measurement of diameter/force may be specific to the measurement location. In yet another example, airflow impedance measurement using a superimposed perturbance could also be used and distinguish proximal and distal airway resistance.

The stimulation member 514 may be any suitable stimulation member configured to stimulate a targeted nerve of an airway. For example, stimulation member 514 may include one or more energy delivery elements that are configured to deliver a non-ablative or non-therapeutic energy. That is, the use of stimulation member 514 may not substantially damage tissues of the body (e.g., little to no healing of stimulated tissues may occur after stimulation by stimulation member 514). In one example, stimulation member 514 may deliver a stimulation with an amplitude of about 10 volts, or from 0.2 to 25 volts. The stimulation may be characterized by brief pulse trains (e.g., about 1-25 Hz and 0.2 to 2 ms pulse duration for less than about ten seconds). In some examples, stimulation member 514 may deliver other suitable modalities of energy, such as, e.g., ultrasound energy or magnetic fields to stimulate neural activity. In alternative examples, features of stimulation member 514 may be combined with features of therapy member 510. For example, stimulation member 514 may be configured to deliver both non-ablative (or non-therapeutic) energy in a stimulation mode, while also being able to deliver ablative (or therapeutic) energy in a therapy delivery mode. Therapeutic energy may include energy sufficient to induce a healing response in tissue and/or induce either temporary or permanent effects on tissue. In such an example, therapy member 510 may not deliver therapy, but rather, may serve as a measurement member that, for example, measures characteristics and parameters of an airway. The stimulation member 514 and the therapy member 510 each may be configured to operate in a monopolar mode (with a ground pad disposed elsewhere on the patient), in conjunction with one another (e.g., energy sent from stimulation member 514 to therapy member 510, or vice versa). Stimulation member 514 and therapy member 510 may alternatively operate in a bipolar mode (e.g., two or more separate circuits or electrode surfaces may be disposed on the stimulation member 514 and/or therapy member 510.

Figure 6:
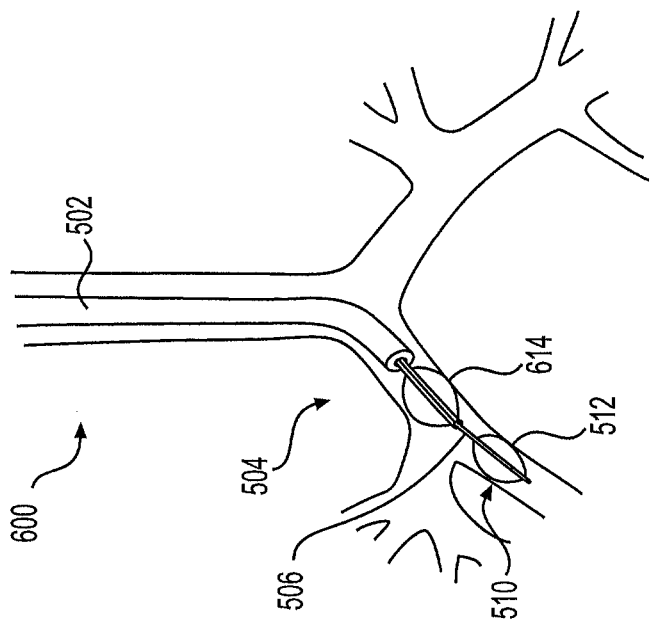
FIG. 6 is an in vivo illustration of a medical device in accordance with another example of the present disclosure.

A medical device 600 is shown in FIG. 6. Medical device 600 may be substantially similar to medical device 500 described with reference to FIG. 5, except that medical device 600 may include a stimulation member 614 instead of a stimulation member 514. Stimulation member 614 may be substantially similar to stimulation member 514, except that stimulation member 614 may be disposed on second elongate member 506 instead of on sheath 516. In the example of FIG. 6, stimulation member 614 may be disposed proximal to therapy member 510.

Figure 7:
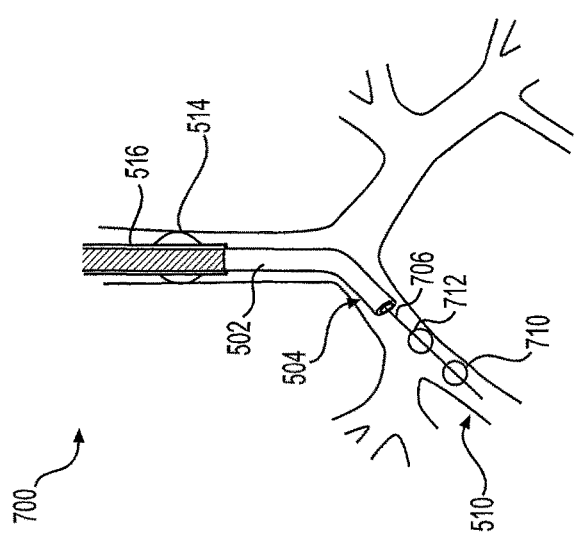
FIG. 7 is an in vivo illustration of a medical device in accordance with another example of the present disclosure.

A medical device 700 is shown in FIG. 7. Medical device 700 may be substantially similar to medical device 500 described with reference to FIG. 5, except that medical device 700 may include a second elongate member 706, a measurement member 710, and an energy delivery member 712, instead of second elongate member 506 and therapy member 510. Measurement member 710 and energy delivery member 712 each may be disposed along second elongate member 706. Stimulation member 514 may be proximal to energy delivery member 712, and measurement member 710 may be distal to energy delivery member 712. In some examples, second elongate member 706 may include one or more flexible and/or articulatable junctions between measurement member 710 and energy delivery member 712 such that energy delivery member 712 may be disposed in a first airway and measurement member 710 may be disposed in a second airway that is distal to the first airway. Measurement member 710 may be an expandable member substantially similar to therapy member 510 described with reference to FIG. 5 except that measurement member 710 may not deliver therapy, but rather, may serve as a measurement member that measures characteristics and parameters of an airway. Energy delivery member 712 may be an expandable member configured to perform the therapy functions (e.g., therapeutic energy delivery) that are performed by therapy member 510. However, it is further contemplated that each of measurement member 710 and energy deliver member 712 may be configured to deliver therapeutic energy and serve as a measurement member.

Figure 8:
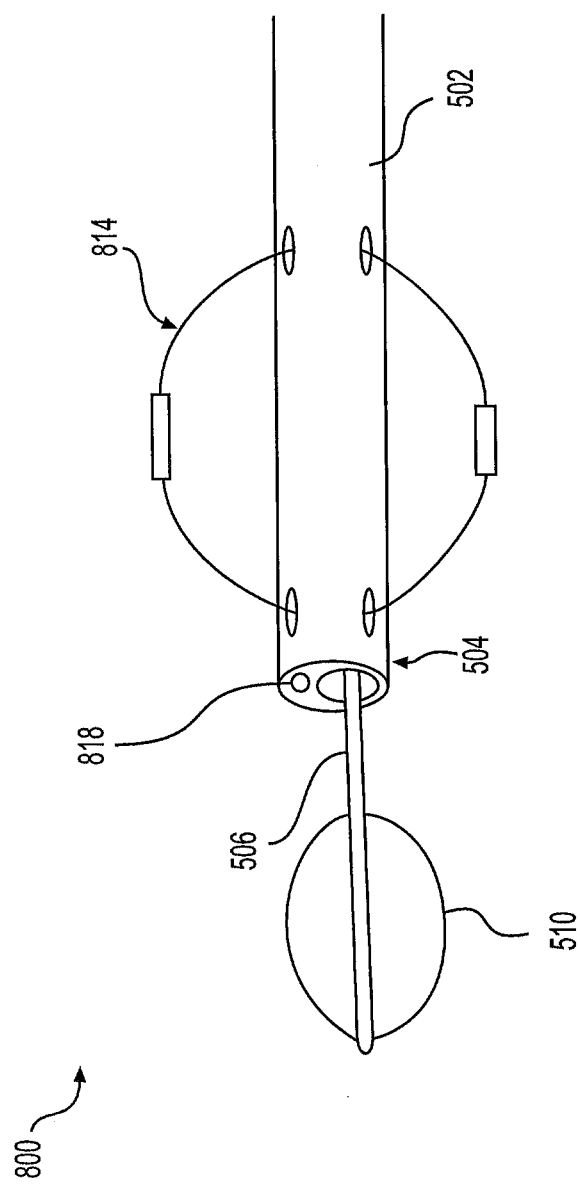
FIG. 8 is a partial side view illustration of a medical device in accordance with another example of the present disclosure.

A medical device 800 is shown in FIG. 8. Medical device 800 may be substantially similar to medical device 500 described with reference to FIG. 5, except that medical device 800 may include a stimulation member 814 instead of a stimulation member 514. Stimulation member 814 may be substantially similar to stimulation member 514, except that stimulation member 814 may be disposed at distal end 504 of first elongate member 502 instead of on sheath 516. In the example of FIG. 8, stimulation member 814 may be disposed proximal to therapy member 510. Medical device 800 may include an imaging device 818 that is configured to measure a parameter of an airway. In some examples, imaging device 818 may be configured to facilitate the measurement of airway contraction and/or airway diameter.

Figure 9:
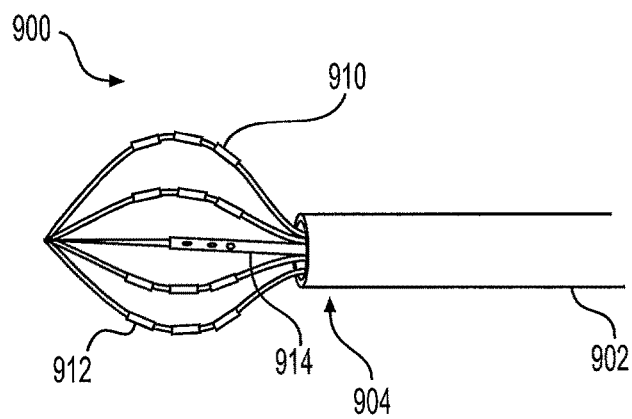
FIG. 9 is a partial side view illustration of a medical device in accordance with another example of the present disclosure.

A medical device 900 is shown in FIG. 9. Medical device 900 may include a first elongate member 902 that is configured to extend from a bronchoscope, endoscope, or the like. A therapy member 910 may be disposed at a distal end 904 of first elongate member 902. Therapy member 910 may be substantially similar to therapy member 510 described with reference to FIG. 5 and may operate in either an energy delivery mode or a measurement mode (similar to therapy member 510 described above). In the example shown in FIG. 9, therapy member 910 may be an expandable basket having a plurality of energy delivery elements 912 that are substantially similar to energy delivery elements 512. Medical device 900 also may include a stimulation member 914 disposed within therapy member 910 or in another suitable location. Stimulation member 914 may be configured to deliver a nerve stimulant to an airway. The nerve stimulant may be any suitable stimulant configured to trigger a nerve to produce a constriction response at or distal to the point where stimulus is introduced to the nerve. For example, the nerve stimulant may be methacholine, histamine, bradykinin, adenosine, mannitol, other suitable agents that elicit neurotransmitter release, and other chemical agent capable of eliciting a bronchoconstrictive response.

Figure 10:
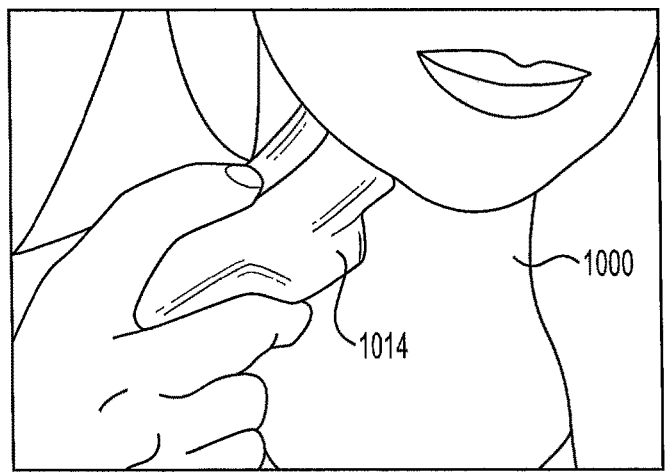
FIG. 10 is a perspective view illustration of a stimulation member in accordance with another example of the present disclosure.

FIG. 10 depicts an alternative example having a stimulation member 1014 that is configured to apply a stimulus to a stimulation location, e.g., a vagus nerve, transcutaneously through the skin of a subject 1000. That is, stimulation member 1014 may be configured to deliver a non-therapeutic pulse or pulses through the skin of subject 1000 without piercing the skin of subject 1000. Alternative examples of the present disclosure also contemplate that stimulation of a target nerve may be achieved percutaneously (e.g., by piercing the skin to stimulate the target nerve). The stimulation member may include a percutaneous needle that has one or more active distal electrode surfaces. The percutaneous needle may be delivered to the region of the vagus nerve by ultrasound, x-ray guidance, laparoscopic techniques, among others, similar to needle injections or needle RF ablations performed in clinical settings. In a monopolar mode, a majority of the outer diameter of the needle may be non-conductive, and only a distal portion of the needle (in contact with or near the nerve) may be conductive. The conductive region may be defined by a lack of insulative material on the outer diameter of the needle. Alternatively, a conductive electrode may be placed through an insulated needle, extending slightly beyond the tip of the insulated needle, serving as an electrode surface for stimulation. Stimulation and/or treatment also may be by other modalities, such as, e.g., acoustic, optical, ultrasound, laser, optogenic, or other modalities.

Alternatively, the stimulation member may be a catheter or lead similar in design to pacing leads used for neuromodulation or cardiac rhythm management. It is further contemplated that a given system may only have stimulation and measurement capability as a diagnostic tool. Alternatively, some devices may only include energy therapy capability and measurement capability, whereby the stimulation may occur naturally (e.g., baseline tone) or via pharmacologic methods.

Figure 11:
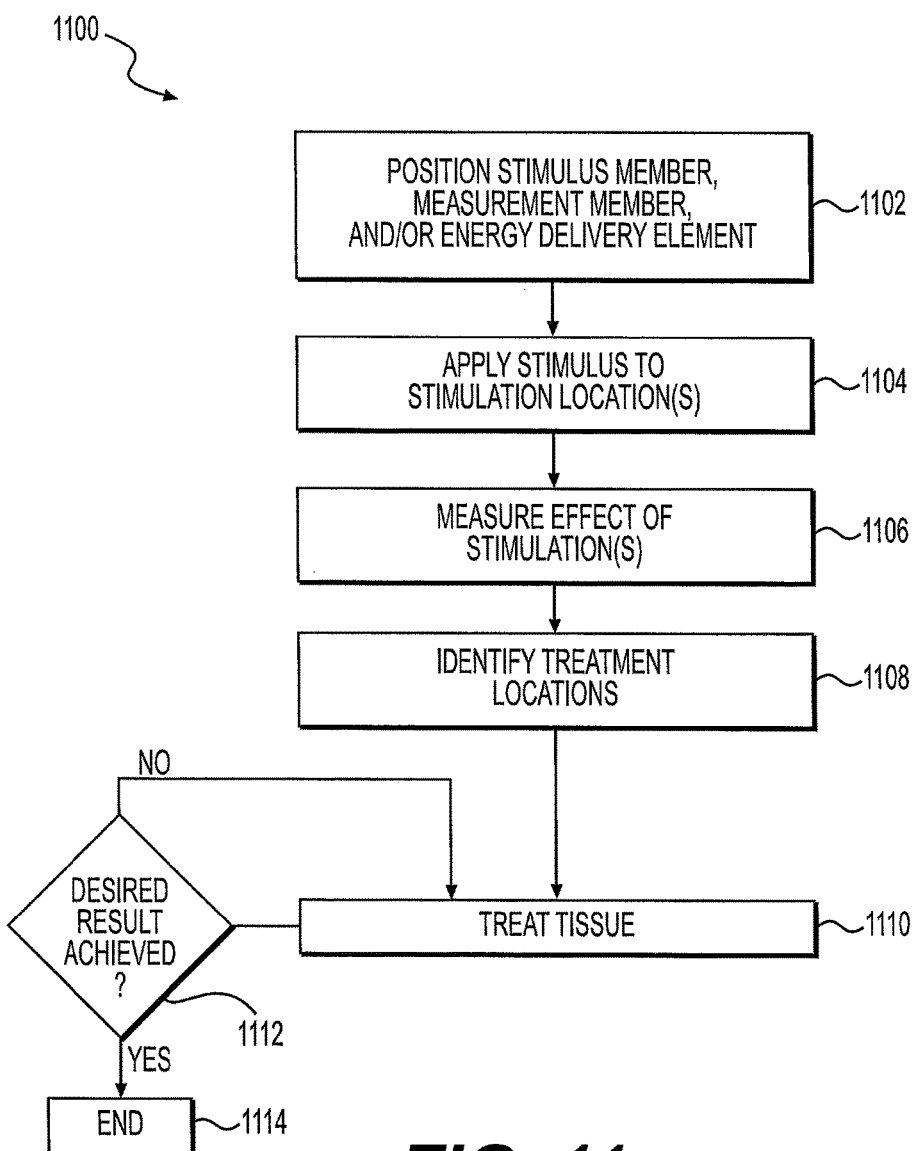
FIG. 11 is a flowchart depicting an exemplary method of the present disclosure.

FIG. 11 is a flow diagram of a method 1100 for identifying treatment locations in a lung. Specifically, as shown in FIG. 10, method 1100 may include a step 1102 where a medical device including one or more of a stimulation member, a measurement member, and an energy delivery element are inserted into an airway. The medical device may include any of medical devices 500, 600, 700, 800, and 900 from FIGS. 5-9. Method 1100 then may proceed to step 1104, where a stimulus may be applied by a stimulation member to a stimulation location (e.g., vagus nerve). The stimulation member may include any one of stimulation members 514, 614, 814, 914, and 1014 from FIGS. 5-10. In one example, the stimulation location may include the vagus nerves in the cervical region (via either transcutaneous or percutaneous stimulation options), or the vagus nerves at a location in the airways such as the trachea or bronchi. Stimulating at certain parameters may drive maximal constriction of the distal airways. The stimulation parameters may be dependent upon the proximity to the efferent (motor) nerve fibers during stimulation. In one example, the parameters may include 10 volts, 200 millisecond pulse width, and 25 Hz frequency to provide beneficial contractile responses when stimulation is delivered directly to the nerve. However, any other suitable parameter alternatively may be utilized, such as, e.g., 0.1 to 25 volts, current up to 20 mA, 10 to 2000 microsecond pulse width, and 10 Hz to 10 KHz frequency.

The stimulation location may be any suitable location within an airway, or along tissues defining or otherwise surrounding an airway such that the stimulus can trigger a nerve response of the target nerve sufficient to cause the constriction of an airway distal to the stimulation location. The stimulation may be performed electrically (such as by placing a device within the airway and stimulating using the settings described herein). Alternatively, or in combination, the stimulation may be artificially induced using an stimulus agent, such as, e.g., methacholine, histamine, bradykinin, adenosine, mannitol, and other suitable agents that elicit neurotransmitter release. Stimulation, non-therapeutic, and/or therapeutic energy also may be by other modalities, such as, e.g., acoustic, optical, ultrasound, laser, optogenic, or other modalities.

Step 1104 also may include applying a stimulus to multiple stimulation locations to increase the number of data points collected. For example, step 1104 may include separately stimulating various stimulation locations while measuring the effect of the separate stimulations at the same distal measurement location. In one example, a first stimulus may be applied to a first stimulation location. Then, a second stimulus may be applied to a second stimulation location separate from the first stimulation location. Step 1104 also may include varying the intensity of the stimulus applied to one or more stimulation locations. For example, a first stimulus applied to a given stimulation location may include a first set of parameters (e.g., power, pulse duration, electrical signals, amplitude, current, pulse, width, frequency, waveform, or the like), while a second stimulus applied to the given stimulation location may include a second set of parameters different from the first set of parameters.

Simultaneous to the stimulation occurring at step 1104, or shortly (e.g., immediately after, for example, 0.001-10,000 seconds, although other suitable times are also contemplated) thereafter, method 1100 may proceed to step 1106, where a measurement member may determine the effect (e.g., a degree of constriction, a diameter measurement, a force measurement, an airflow measurement, an EMG signal, an ENG signal, or the like) of applying a stimulus at the stimulation location. The effect may be measured at the stimulation location and/or at a measurement location distal to the stimulation location. The measurement location may be located in the same airway as the stimulation location, or may be located at an airway that is distal to the stimulation location. For example, the stimulation location may be located in a first or second generation airway, while the measurement location may located in a third or subsequent generation airway, although other suitable combinations are also contemplated. In some examples, a plurality of measurement locations are utilized. For example, one measurement member may be disposed in a distal airway, and another measurement member may be disposed closer to the stimulation member to measure proportions of distal versus central airway constriction. In another example, one measurement member may be disposed in each lobe to measure which lobe is most severely affected by a given stimulus. Treatments then may be tailored for a specific lobe or for several lobes. In one example, the stimulation locations may be positioned at or near the carina. The stimulation location may be in the first to third generation (or even more distal) airways. Other examples of suitable stimulation locations include the pulmonary nerve plexuses at the first bronchi at the hilum of the lung. The stimulation location and measurement location may be any suitable distance from one another, such as, e.g., 0.5 to 2 cm from one another, although other suitable distances are also contemplated. Shorter distances between the sites may minimize the length of device that would need to extend beyond a bronchoscope during use, for example.

The parameters to be measured in accordance with the methods described herein may be any parameter that is an indicator of or associated with symptoms of OPD. For example, the parameter may be a measure of pulmonary function values, a measure of the contractile force at which the airway contracts, degree of airflow within the airway, degree of contraction of the airway during or after stimulation of the airway, and/or degree of wheezing at a particular location, etc. The measurement member may include any one of therapy member 510, measurement member 710, or 910 of FIGS. 5-9. Alternatively, an imaging device (e.g., imaging device 818 of FIG. 8) may take a first image of an airway at a measurement location. Next, a stimulation may be applied to a stimulation location that is proximal to the measurement location to induce contraction of the airway encompassing the distal measurement location. Imaging device 718 then may obtain a second image of the airway for comparison with the first image to determine the degree of contraction at the measurement location as a result of the stimulation at the stimulation location.

Once the effect of stimulation is determined at step 1106, method 1100 then may proceed to step 1108 to identify one or more treatment locations by comparing the measured parameters to known or studied parameters, or to one another. In some examples, selecting treatment locations may include selecting stimulation locations that resulted in an effect on distal measurement locations that meet or exceed specific criteria. For example, selecting a treatment location may include identifying stimulation locations that caused a minimum threshold constriction response in one or more different distal airways, and treating those stimulation locations. For example, if the parameter comprises measuring contractile force or the amount of contraction in an airway at the measurement location or distal to the stimulation location, then stimulation locations causing the most constriction in the distal airways may be selected as treatment locations. Alternatively, measurement locations experiencing the most constriction may be selected as treatment locations.

Alternatively, or in combination, identification of treatment locations may include selecting the stimulation and/or measurement locations resulting in the most significant measured parameters relative to other stimulation and/or measurement locations. In another example, the parameters may be ranked in a desired order of value, and those sites that are believed to provide the most benefit may be treated. For example, a percentage (e.g., top ten percent) of stimulation sites causing the most contraction in the distal airways may be selected for treatment, or a top percentage of measurement sites experiencing the most contraction may be selected for treatment. In another example, selection of stimulation and/or measurement locations may include titrating up or gradually increasing the stimulation parameters until a given threshold (e.g., current, voltage, chemical dose, or other parameter described herein) is surpassed at the measurement location. In some examples, the threshold may represent a 25% or other suitable change in airflow resistance. In this example, the stimulation location(s) which required the least amount of stimulation (e.g., lowest current or voltage) to produce a response that exceeded the threshold may be the location(s) to target for energy therapy. The locations selected may represent the most hyperresponsive locations in need of treatment.

It is also contemplated that the treatment locations may be offset and/or distal to the stimulation locations that, e.g., cause the highest level of contraction in the distal airways. One example of when energy therapy may be distal to the stimulation location includes when the stimulation location is located proximally in the cervical region to drive a contractile response in the airways (the measurement location). In this example, the treatment location may be located in the airways, in close proximity to (or at) the location of the measurement location, not in the cervical region where the vagus was stimulated. In some examples, where the medical device includes stimulation, energy delivery, and measurement members at the distal end of the device, the various members may be located in close proximity to one another. This may allow for the use of a relatively compact device that does not require significant extension beyond the distal end of, e.g., a bronchoscope. This design also may enable a substantial entirety of the medical device to remain in the field of view of most anatomies. The treatment location may be located at the stimulation location. Alternatively, the treatment location may be distal to the stimulation location. In some examples, the therapeutic energy may have an irreversible effect on the airway tissue. The irreversible effect may add increased noise to data analysis. For example, while energy delivery exactly at the stimulation location may cause a reduced response at the measurement location due to a given stimulus compared to pre-therapy levels. However, if the energy therapy was delivered in the exact same location as the stimulation, it may be difficulty to accurately determine if the change in response to same stimulation is due to the therapeutic effect of the delivered therapeutic energy on the nerves, or due to other acute changes in tissue around the nerves affecting the energy transfer from the device during stimulation (e.g., altered impedance in the location due to tissue changes). If the energy therapy is delivered distal to the stimulation site (e.g., 0.5 cm to 2 cm, or another suitable distance), then it may be easier to determine that the therapeutic effect is due to denervation.

Method 1100 then may proceed to step 1110, where the identified treatment sites may be treated by, e.g., an energy delivery element. The energy delivery element may include any one of therapy member 510, energy delivery member 712, and therapy member 910 of FIGS. 5-9. The treatment sites may be treated in any suitable manner to reduce airway constriction at or distal to the treatment location. When therapeutic energy being applied at the treatment location is RF (or electrical) energy, the energy may be applied for a length of time in the range of about 0.1 seconds to about 600 seconds. In one example, a power source may be capable of delivering about 1 to 100 watts of energy, and may possess continuous flow capability. The tissues defining a lung airway may be maintained at a temperature that is lesser than, equal to, or greater than ambient body temperature. In one example, the tissues may be maintained at at least about 60° C., between 70° C. to 95° C., and/or between 70° C. to 85° C. The power-level may generally range from about 0-30 W, or another suitable range. In some examples, the power source may operate at up to a 75° C. setting. In some examples, energy may be delivered in discrete activations of, e.g., 5 to 10 seconds per activation. The frequency of the energy may be from 300 to 1750 kHz.

It should be noted that, in at least some examples, other suitable values for energy delivery times, wattage, airway temperature, electrode temperature, and frequency are also contemplated.

Once the identified treatment locations are treated (e.g., ablated), method 1100 then may proceed to step 1112, where an efficacy of treatment may be determined. For example, if the treatment step 1110 is determined to produce a desired result, the treatment and method may end at step 1114. However, if the treatment step is not determined to have produced the desired result, the method may return to step 1110 for further treatment and ablation. Efficacy of treatment may be determined by re-stimulating the stimulation locations and measuring the corresponding distal airway contraction. In some examples, a desired result may be based on a desired level of contraction in a distal airway in response to a given stimulus at a stimulation location. It is also contemplated that the desired result may be based on any of the other measured parameters discussed herein, e.g., a desired airflow, airway diameter, force level, electrical signals, or the like. An operator may re-ablate the treatment location/stimulation location until the desired result is achieved in the lung.

Any aspect set forth in any example may be used with any other example set forth herein. The devices and apparatus set forth herein may be used in any suitable medical procedure, and may be advanced through any suitable body lumen and body cavity. For example, the apparatuses and methods described herein may be used through any natural body lumen or tract, or through incisions in any suitable tissue.

It will be apparent to those skilled in the art that various modifications and variations can be made in the disclosed systems and processes without departing from the scope of the disclosure. Other examples of the disclosure will be apparent to those skilled in the art from consideration of the specification and practice of the disclosure disclosed herein. It is intended that the specification and examples be considered as exemplary only. The following disclosure identifies some other exemplary examples.

We claim:

1. A method of treating a lung, comprising:
   applying stimulus to a nerve at a stimulation location;
   measuring an effect of the stimulus on an airway of the lung, the airway being spaced apart from or distal to the stimulation location;
   selecting a treatment location in the lung distal to the stimulation location when the measured effect of the stimulus on the airway is greater than a threshold value; and
   applying therapeutic energy to lung tissue at the treatment location.

2. The method of claim 1, wherein the nerve regulates lung airway constriction.

3. The method of claim 1, wherein the nerve is a vagus nerve.

4. The method of claim 3, wherein the vagus nerve is stimulated at a location distal to cardiac branches of the vagus nerve.

5. The method of claim 1, wherein the stimulus is an agent configured to activate the nerve to induce constriction of the lung airway.

6. The method of claim 5, wherein the agent is capsaicin.

7. The method of claim 1, wherein measuring the effect of the stimulus on the airway includes measuring an amount the airway constricts in response to the stimulus.

8. The method of claim 1, wherein the treatment location is proximal to the airway.

9. The method of claim 1, wherein the threshold value includes one or more of a minimum contraction level, a minimum force level, a minimum airway diameter, and a minimum airflow value.

10. The method of claim 1, further including applying an additional stimulus to the stimulation location after applying therapeutic energy to the treatment location, and measuring the effect of the additional stimulus on the airway.

11. The method of claim 10, further including re-applying therapeutic energy to the treatment location if the measured effect of the additional stimulus exceeds the threshold value.

12. The method of claim 1, wherein the treatment location is 0.5 to 2.0 cm distal to the stimulation location.

13. The method of claim 1, wherein the stimulation location is within the lung.

14. The method of claim 1, wherein applying stimulus to a nerve at a stimulation location includes applying stimulus to a first airway of the lung, and measuring an effect of the stimulus on an airway of the lung includes measuring an effect of the stimulus on a second airway and a third airway of the lung, wherein the second airway and the third airway are of a higher generation than the first airway.

15. The method of claim 14, further including applying therapeutic energy to each of the first airway, the second airway, and the third airway.

16. The method of claim 1, wherein applying stimulus to a nerve at a stimulation location includes applying a stimulus to a carina, and measuring an effect of the stimulus on an airway of the lung includes measuring an effect of the stimulus on a first lobe of the lung and on a second lobe of the lung, and wherein therapeutic energy is applied in only one of the first lobe and the second lobe of the lung.

17. The method of claim 1, wherein applying stimulus to a nerve at a stimulation location includes applying, at different times, stimulus to a plurality of stimulation locations, and during each stimulation, the method includes simultaneously measuring an effect of a respective stimulus on each of a plurality of airways, and selecting a treatment location includes selecting only some of the stimulation locations and only some of the measurement locations to receive therapeutic energy.

18. The method of claim 1, wherein applying therapeutic energy to lung tissue at the treatment location causes denervation of both afferent and efferent nerves.

19. The method of claim 1, wherein the treatment location is 0.5 to 2.0 cm distal to the stimulation location, the stimulation location is within the lung, and applying therapeutic energy to lung tissue at the treatment location causes denervation of both afferent and efferent nerves.

20. The method of claim 19, wherein the agent is capsaicin.

* * * * *